United States Patent [19]

Levine

[11] 4,155,945

[45] May 22, 1979

[54] CONTINUOUS PROCESS FOR DEHYDRATION OF TERTIARY BUTYL ALCOHOL

[75] Inventor: Ralph Levine, Freehold, N.J.

[73] Assignee: Cities Service Company, Tulsa, Okla.

[21] Appl. No.: 927,215

[22] Filed: Jul. 24, 1978

[51] Int. Cl.² ............................................. C07C 1/24
[52] U.S. Cl. .................................................. 585/639
[58] Field of Search ........................................ 260/682

[56] References Cited

U.S. PATENT DOCUMENTS

| | | | |
|---|---|---|---|
| 3,256,250 | 6/1966 | Frilette | 260/682 |
| 3,510,538 | 5/1970 | Rosenthal | 260/682 |
| 4,065,512 | 12/1977 | Cares | 260/682 |

Primary Examiner—C. Davis
Attorney, Agent, or Firm—Richard D. Stone

[57] ABSTRACT

Tertiary butyl alcohol, containing some water, is dehydrated to isobutylene in the presence of a catalyst and a hydrocarbon which forms an azeotrope with water. Isobutylene, water, and the hydrocarbon are passed through a condenser to a phase separator from which isobutylene is recovered, preferably as a vapor phase, hydrocarbon is recycled to the dehydration zone, and a water phase removed from the process. The alcohol feed point location is the phase separator. A significant fraction of water contained in the tertiary butyl alcohol feed can be removed inexpensively, by phase separation, in the separator, to minimize the amount of water entering the dehydration zone.

9 Claims, 1 Drawing Figure

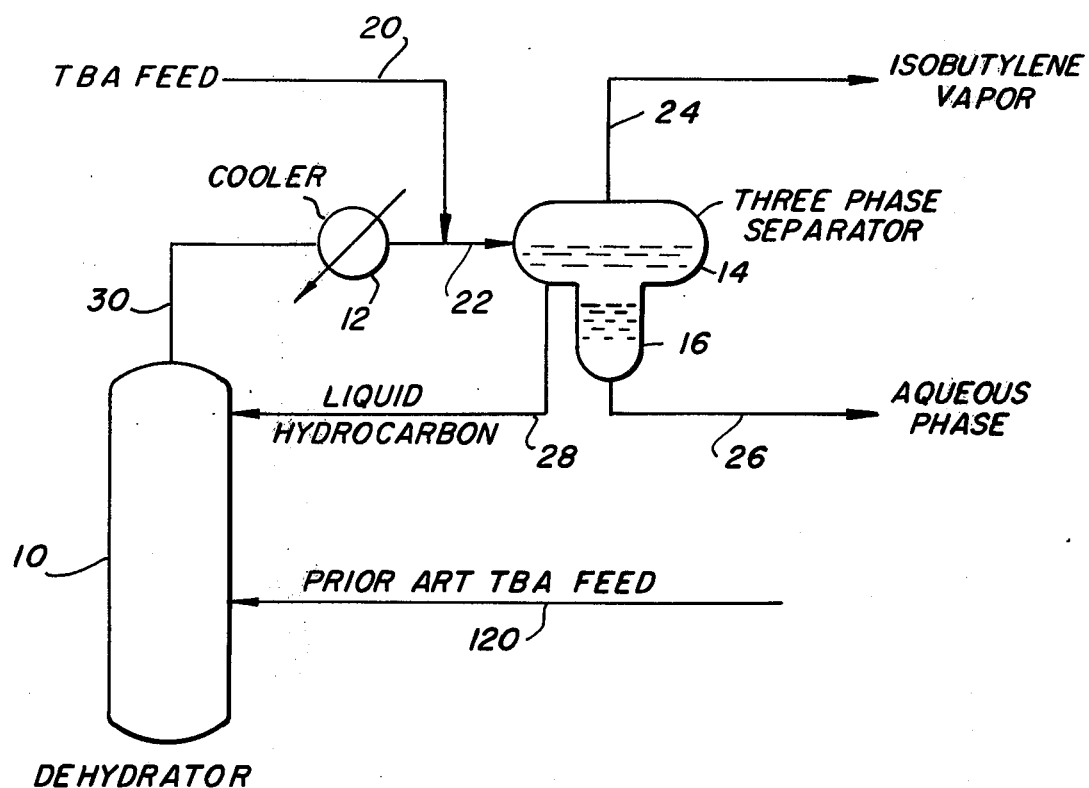

CONTINUOUS PROCESS FOR DEHYDRATION OF TERTIARY BUTYL ALCOHOL

BACKGROUND OF THE INVENTION

FIELD OF THE INVENTION

This invention relates to a method in the continuous dehydration of tertiary butyl alcohol using catalyst wherein water formed in the dehydration reaction is continuously removed from the reaction zone.

The dehydration of tertiary butyl alcohol, TBA, to form isobutylene is well known. The reaction is a relatively simple one to promote, high temperature alone will convert tertiary butyl alcohol to isobutylene, though it is usually preferred to use a catalyst.

U.S. Pat. No. 3,510,538 (U.S. Class 260-682), the teachings of which are incorporated by reference, discloses a continuous process for dehydration of tertiary butyl alcohol which uses as an acid-acting catalyst cation exchange resins, preferably the sulfonic acid type cation exchange resins.

This reference also discloses the use of benzene in the dehydration zone. The benzene forms an azeotrope with the water produced during dehydration of TBA. The benzene-water azeotrope and produced isobutylene are removed as a vapor from the dehydration zone and the vapors cooled to permit condensation of benzene and water but not isobutylene. A water phase is withdrawn from the process, benzene is recycled to the dehydration zone, and isobutylene product is recovered as a vapor.

The process described in that patent is reasonably satisfactory, but is not very efficient in handling TBA feed streams which already contain a significant amount of water.

TBA is usually produced by hydrating isobutylene in the presence of sulfuric acid catalyst, or other acid-acting catalyst such as sulfonic acid type cation exchange resins. It is inherent in many of these processes that the TBA produced contains a substantial amount of water. Water and TBA form an azeotrope, so the only way to remove water from TBA by distillation is to add an additional azeotrope forming agent, such as benzene, to separate water and TBA. Significant energy must be used to vaporize the water, and the material forming an azeotrope with the water.

In the days of inexpensive energy, fractionation costs were relatively low, and petrochemical manufacturers could tolerate the increased utilities demand caused by watery TBA feed to a TBA dehydrator. There was also no practical way known, until now, to remove the water which was present in the TBA feed to the dehydrator, so removal of water was simply accepted as part of the process.

SUMMARY OF THE INVENTION

We have discovered that a significant portion of the water in the TBA feed can be removed merely by changing the location of the feed point to the process. Adding the wet TBA feed downstream of the dehydrator and into the hydrocarbon phase obtained from a phase separator results in significant water removal from TBA feed. The TBA dissolves in the hydrocarbon phase, forcing most of the TBA's water content to merge into the separate water phase. This can be accomplished in the conventional three phase separator used in this process.

This was a surprising phenomenon, that adding TBA feed to a vessel containing a free water phase would dry the TBA.

Accordingly, the present invention provides a process for catalytically dehydrating tertiary butyl alcohol containing water dissolved therein to isobutylene by adding the alcohol to a reaction zone containing catalyst and a hydrocarbon azeotrope forming agent. Isobutylene and water are produced in the reaction zone and isobutylene and a hydrocarbon-water azeotrope are removed as a vapor fraction from the reaction zone. The vapor fraction is cooled and passed through a phase separator, the azeotrope forming agent is collected as a liquid and recycled to the process and water of hydration and water dissolved in the alcohol feed is removed as an aqueous phase wherein the improvement comprises contacting the tertiary butyl alcohol feed with azeotrope forming medium prior to recycle of the medium to the reaction zone.

BRIEF DESCRIPTION OF DRAWING

The drawing is a simplified schematic of one preferred embodiment of the present invention showing a dehydrator and three phase separator.

DETAILED DESCRIPTION OF INVENTION

The catalysts which can be used include cation exchange resins, sulfuric acid, molecular sieves, etc. In fact, any catalyst can be used which will promote dehydration of TBA. Toluene sulfonic acid is preferred.

The azeotrope forming agent must be capable of forming an azeotrope with water at the conditions experienced in the dehydrator, and must be capable of dissolving a significant portion of TBA at conditions experienced in the phase separator. Aliphatic and aromatic hydrocarbons having boiling points ranging from 60°-140° C. are suitable, with benzene, toluene and xylenes giving especially good results. Paraxylene is the preferred azeotrope forming agent, however, processes using conventional azeotrope forming agents such as benzene can also benefit from the practice of the present invention.

Feed streams which can be used in the present invention include any conventional sources of TBA which contain water. If anhydrous TBA is available, it would be pointless to practice the present invention. Typical water contents of TBA feedstocks range from 3 to 60 weight percent $H_2O$, with 15 to 40 weight percent water being common.

In the past, efforts were made to operate TBA production units to produce a relatively dry TBA stream, because of the expense involved in removing water from the TBA produced. With the practice of the present invention, the amount of water which can be tolerated in the TBA product increases significantly, which may shift the economics of the TBA production step to result in significant increases in water content.

DESCRIPTION OF DRAWING

The drawing is a simplified flow diagram in which pumps, control valves, heaters and similar items are not shown.

Dehydrator 10 can be a conventional reaction vessel containing a solid resin catalyst, or other catalyst. Preferably dehydrator 10 contains p-toluene-sulfonic acid, PTSA, or a mixture of PTSA and O-toluene-sulfonic acid, OTSA.

Line 120, indicated as prior art TBA feed, is the feed point location used in the prior art. In the present invention, TBA feed is added to the unit via lines 20 and 22 and three phase separator 14. Most of the TBA is retained in the hydrocarbon phase and is withdrawn from separator 14 via line 28 and charged to dehydrator 10.

Removed as a vapor stream from dehydrator 10 via line 30 is a mixture of isobutylene, water, and azeotrope forming agent, preferably paraxylene. The vapors are cooled in cooler 12 to 20° to 40° C. and charged via line 22 to three phase separator 14. Isobutylene is removed as a vapor phase via line 24. Water, and some dissolved TBA, is removed from leg 16 via line 26. This aqueous phase may be sent to a conventional distillation column wherein further separation of TBA from water may occur. Conventional fractionation is not as expensive as azeotropic distillation because each weight of water requires five or six weights of paraxylene in azeotropic distillation. Conventional fractionation will not completely dry a wet TBA fraction, however. Alternatively, this aqueous phase may be recycled to a TBA production unit to satisfy all or part of the water requirement of that process.

A frequently encountered water concentration will be 88 weight percent TBA and 12 percent water, this composition being an azeotrope which forms at atmospheric pressure. Depending on the type of product separation facilities used in the TBA production unit, significantly higher water levels may be obtained, if, for instance, an unrefluxed distillation column is used to recover TBA product.

The temperature and pressure in the dehydrator should be sufficient to cause water to boil the liquid therein. Bottoms temperatures of 80° to 200° C. are possible under a vacuum or relatively high pressure. Operation at atmospheric pressure is possible, but then refrigeration will be needed to cool the overhead vapor products sufficiently to cause the water and azeotrope forming agent to condense. Isobutylene produced, at atmospheric pressure, must be cooled to −6° C. to be condensed. Operation at atmospheric pressure requires a temperature of about 115° C. in the dehydration zone when paraxylene is used as the azeotrope forming agent. Operation at 4 to 6 atmospheres pressure in the dehydration zone will permit use of cooling water at 20°–40° C. to condense isobutylene.

The point of addition of wet TBA feed is based on several factors. Adding wet feed upstream of cooler 12 will reduce the amount of cooling water required in cooler 12, and ensure very good contact of incoming wet feed with vapors from the dehydrator. Addition of wet feed downstream of cooler 12 minimizes the amount of material passing through the cooler, and still ensures relatively good contact of feed with material from dehydrator 10. Direct addition of wet feed to the three phase separator is possible, but not preferred unless some mixing means is provided so that wet feed will adequately contact incoming hydrocarbon. The optimum feed point location, from a strict water removal standpoint, would be after some phase separation had occurred in three phase separator. In this mode of operation, hydrocarbon is withdrawn from three phase separator 14 via line 28, mixed with wet TBA feed from line 20, and the mixture passed through a liquid/liquid separator, not shown. This mode of operation would minimize TBA losses to the aqueous phase, as most of the water produced in the dehydrator would be removed in three phase separator 14. The hydrocarbon feed from separator 14 would still be saturated with water, but that is a miniscule amount compared to the amount generated and removed by azeotropic distillation from the dehydrator.

It is believed that the slight amount of TBA loss to the aqueous phase in the three phase separator will not justify the capital expense of installing an extra liquid separator between three phase separator 14 and dehydrator 10.

It would also be possible, but usually not worth the expense, to incorporate additional heat exchange equipment in the line returning hydrocarbon to dehydrator 10. If this material were cooled substantially, more water could be removed, but usually the extra equipment would not be justified.

Similarly, it would be possible to operate three phase separator 14 as a vapor/liquid separator followed by a liquid/liquid separator operating on the liquid phase from the two phase separator.

EXAMPLE 1

To show the effect of mixing wet TBA streams with xylene, 100 grams of TBA solution was added to varying amounts of a xylene fraction. Paraxylene is the preferred azeotrope forming agent, but mixed xylenes were used in this test. The TBA and xylene were added, at room temperature, to a flask and stirred for 2 to 5 minutes, and then allowed to settle for 20 to 30 minutes. In most instances, an aqueous phase formed on the bottom of the flask, with a hydrocarbon phase above it. These phases were analyzed. The results when 50 grams of xylene were added are reported in Table 1.

TABLE 1

| | | | |
|---|---|---|---|
| TBA.g | 63 | 73 | 84 |
| H$_2$O.g | 37 | 27 | 16 |
| Total.g | 100 | 100 | 100 |
| Aqueous phase: | | | |
| TBA | 6.4 | 3.2 | — |
| H$_2$O | 22.8 | 11.3 | — |
| Hydrocarbon phase: | | | |
| TBA | 56.6 | 69.8 | — |
| H$_2$O | 14.2 | 15.7 | — |
| Xylene | 50 | 50 | — |

No phase separation occurred in the test using 84 wt% TBA.

These tests were repeated, with 100 g mixed xylenes. The results are reported in Table II.

TABLE II

| | | | |
|---|---|---|---|
| Aqueous phase: | | | |
| TBA | 6.3 | 4.2 | 1.6 |
| H$_2$O | 27.7 | 17.5 | 5.9 |
| Hydrocarbon phase: | | | |
| TBA | 56.7 | 68.8 | 82.4 |
| H$_2$O | 9.3 | 9.5 | 10.1 |
| Xylenes | 100 | 100 | 100 |

These tests were again repeated, with 150 g mixed xylenes. The results are reported in Table III.

TABLE III

| | | | |
|---|---|---|---|
| Aqueous phase: | | | |
| TBA | 6.6 | 4.9 | 2.4 |
| H$_2$O | 29.2 | 19.7 | 9.2 |
| Hydrocarbon phase: | | | |
| TBA | 52.5 | 66.3 | 81.1 |
| H$_2$O | 7.8 | 7.3 | 6.8 |
| Xylenes | 150 | 150 | 150 |

EXAMPLE 2

This example is an example of the prior art way of adding wet TBA solution to a dehydrator.

A distillation flask with a heating element surrounding it contained 130 g of mixed xylenes and 15 g PTSA. The PTSA catalyst formed a separate liquid phase in the bottom of the flask. Some of the PTSA dissolves in the xylene fraction, and it is believed that this dissolved PTSA functions as the catalyst.

The temperature was maintained at 115° C. Wet TBA solution was added directly to the flask. Power input was constant. Temperature was maintained constant by adding TBA to maintain constant temperature. Adding a lot of wet TBA reduced the temperature, so TBA addition would be increased or decreased to maintain 115° C. These tables are roughly based on constant heat input to the system. Table IV shows operation at 115° C., while Table V shows operation at 125° C.

TABLE IV

| Conditions | Temperature 115° C. Powerstat Setting 85 130 g Xylene 15 g PTSA Feed added directly to dehydrator | | | |
|---|---|---|---|---|
| Feed: | | | | |
| wt % TBA | 97 | 85 | 77 | 66 |
| wt % H$_2$O | 3 | 15 | 23 | 34 |
| g/min TBA dehydrated | 1.87 | 1.51 | 1.04 | 0.89 |
| TBA in aqueous phase in overhead receiver, wt % | 10.8 | 8.0 | 11.3 | 9.0 |

TABLE V

| Conditions | Temperature 125° C. Powerstat Setting 85 130 g xylene 15 g TSA Feed added directly to Dehydrator | | | |
|---|---|---|---|---|
| Feed: | | | | |
| wt % TBA | 97 | 85 | 77 | 66 |
| wt % H$_2$O | 3 | 15 | 23 | 34 |
| g/min TBA dehydrated | 1.6 | 1.12 | 0.92 | 0.80 |
| TBA in aqueous phase, in overhead receiver, wt % | 7 | 8.5 | 10 | 9.5 |

The rate of TBA dehydration, g/min, was determined by measuring the rate of isobutylene production.

It was surprising that the rate of dehydration of TBA decreased at a higher temperature. This simply meant that to run the whole system at 125° C. took more power than to operate it at 115° C., so less TBA was produced for the same power input. This is mirrored in the real world, in that less work is required for low temperature dehydration as opposed to high temperature dehydration. The extra heat input required at the high temperature goes into hot overhead vapors, which heat is then lost, or perhaps recovered to some extent, in subsequent heat exchange with cooling water or other process fluids.

EXAMPLE III

This is an example of the present invention. TBA was not added directly to the dehydration flask, but was added to the overhead receiver. Most of the TBA dissolved in the xylene which was refluxed to the dehydration reactor. TBA feed entered the dehydration reactor with the xylene reflux. Most of the water in the wet TBA feed entered the aqueous phase in the overhead receiver, and was removed from the system. A minor amount of TBA from the feed dissolved in the water phase, and was removed from the system.

TABLE VI

| | (Invention) | |
|---|---|---|
| Conditions | Temperature 115° C. Powerstat Setting 85 130 g xylene 15 g TSA Feed added to Dehydrator Overhead receiver, | |
| Feed: | | |
| TBA, wt % | 84 | 63 |
| H$_2$O | 16 | 37 |
| g / min TBA dehydrated | 1.27 | 1.17 |
| TBA in Aqueous phase, wt % | 12 | 13 |
| TBA in Xylene recycle | 32 | 52 |
| Conditions: | Temperature 125° C. Powerstat Setting 85 | |
| g / min TBA dehydrated | * | 1.09 |
| TBA in Aqueous phase, wt % | * | 12 |
| TBA in Xylene recycle | * | 31 |

* Not Measured

EXAMPLE IV

Example III was repeated, except that an underflow weir was placed in the overhead receiver to minimize the amount of physical entrainment of free water in the xylene recycle stream.

TABLE VII

| | (Invention) | |
|---|---|---|
| Conditions: | Temperature 115° C. Powerstat Setting 105 130 g m Xylene 15 g TSA Feed added to dehydrator overhead receiver, weir provided to minimize H$_2$O entrainment dehydrator. | |
| Feed: | | |
| TBA, wt % | 84 | 63 |
| H$_2$O, wt % | 16 | 37 |
| g / min TBA dehydrated | 2.76 | 2.16 |
| TBA in Aqueous phase, wt % | 12 | 13 |
| TBA in Xylene recycle | 38 | 44 |
| Conditions: | Temperature 125° C. Powerstat Setting 105 | |
| g / min TBA dehydrated | 2.8 | 2.1 |
| TBA in Aqueous phase, wt % | 11 | 12 |
| TBA in Xylene recycle, wt % | 39 | 33 |

Based on laboratory tests, excellent phase separation occurs between the aqueous and hydrocarbon phases within about five minutes. Commercially this would be very easy to attain, as overhead receivers must be significantly oversized to accomodate temporary interruptions of product withdrawal, i.e., the residence time in vessels in most refineries and petrochemical plants is between 15 minutes and one hour. Phase separation should not be a problem.

Analysis of the mixed xylene solution used in the dehydration of TBA showed that about 40% of the mixed xylenes became butylated after many uses. The butylation appeared to occur almost exclusively on the orthoxylene and metaxylene. Paraxylene was not alkylated and is, therefore, the preferred solvent. Toluene, ethylbenzene and xylenes other than paraxylene are expected to react or alkylate. Such alkylation is undesirable because it changes the character of the azeotrope forming agent and consumes TBA without producing isobutylene. Alkylation may result in an azeotrope forming agent which attains so high a molecular weight that it is difficult to vaporize or forms tar. Any increase in weight of azeotrope forming agent is also undesirable in that the heavier material will require more energy to vaporize and subsequently cool than the starting xylene material. This would increase the energy consumption of the process without increasing product purity or production rates.

I claim:

1. In a process for catalytically dehydrating tertiary butyl alcohol containing water dissolved therein to isobutylene by adding said alcohol to a reaction zone containing catalyst and a hydrocarbon azeotrope forming agent, isobutylene and water are produced in the reaction zone and isobutylene and a hydrocarbon-water azeotrope are removed as a vapor fraction from the reaction zone, said vapor fraction is cooled, and passed through a phase separator, the azeotrope forming agent is collected as a liquid and recycled to the process and water of hydration and water dissolved in the alcohol feed is removed as an aqueous phase wherein the improvement comprises contacting the tertiary butyl alcohol feed with azeotrope forming medium prior to recycle of said medium to said reaction zone.

2. Process of claim 1 wherein the catalyst is an acid acting substance.

3. Process of claim 1 wherein the catalyst is a mixture of p-toluene sulfonic acid and o-toluene sulfonic acid.

4. Process of claim 1 wherein the azeotrope forming agent is selected from the group of benzene, toluene, and xylenes.

5. Process of claim 1 wherein the azeotrope forming agent is paraxylene.

6. Process of claim 1 wherein the catalyst is a resin sulfonic acid.

7. Process of claim 1 wherein the alcohol feed is added to the vapor from the reaction zone before the vapor is cooled.

8. Process of claim 1 wherein the alcohol feed is added to the cooled vapor from the reaction zone before the vapor enters a phase separator.

9. Process of claim 1 wherein the alcohol feed is added to the azeotrope forming agent after the water produced in the dehydration reaction has been removed from said agent by phase separation and the resulting mixture of alcohol feed and agent is again subjected to phase separation.

* * * * *